(12) United States Patent
Kikuchi

(10) Patent No.: US 10,451,503 B2
(45) Date of Patent: Oct. 22, 2019

(54) RADIOGRAPHY IMAGE PHOTOGRAPHING DEVICE AND RADIOGRAPHY IMAGE PHOTOGRAPHING SYSTEM

(71) Applicant: KONICA MINOLTA, INC., Chiyoda-ku, Tokyo (JP)

(72) Inventor: Ryouhei Kikuchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 140 days.

(21) Appl. No.: 15/828,863

(22) Filed: Dec. 1, 2017

(65) Prior Publication Data

US 2018/0156680 A1    Jun. 7, 2018

(30) Foreign Application Priority Data

Dec. 2, 2016 (JP) ................... 2016-235248

(51) Int. Cl.

| | |
|---|---|
| *H01J 31/49* | (2006.01) |
| *G01L 5/00* | (2006.01) |
| *G01T 1/00* | (2006.01) |
| *G01P 1/12* | (2006.01) |
| *G01P 15/08* | (2006.01) |
| *A61B 6/00* | (2006.01) |
| *G01P 15/18* | (2013.01) |

(52) U.S. Cl.
CPC ............ *G01L 5/0052* (2013.01); *G01P 1/127* (2013.01); *G01P 15/0891* (2013.01); *G01T 1/00* (2013.01); *A61B 6/4233* (2013.01); *A61B 6/4283* (2013.01); *A61B 2562/0219* (2013.01); *G01P 15/18* (2013.01)

(58) Field of Classification Search
CPC .... G01L 5/0052; G01P 1/127; G01P 15/0819; G01P 15/18; G01T 1/00; A61B 6/4233; A61B 6/4283; A61B 2562/0219
See application file for complete search history.

(56) References Cited

U.S. PATENT DOCUMENTS 9,551,730 B2 * 1/2017 Chau et al. ............. G01P 15/18
73/152.46

FOREIGN PATENT DOCUMENTS

| JP | 2011067334 A | * 4/2011 | ............... A61B 6/00 |
|---|---|---|---|
| JP | 2016001128 A | 1/2016 | |

* cited by examiner

*Primary Examiner* — Kiho Kim
(74) *Attorney, Agent, or Firm* — Cantor Colburn LLP

(57) ABSTRACT

A radiography image photographing device includes: a sensor panel in which a plurality of radiation detection elements is arrayed two-dimensionally; a housing that houses the sensor panel; a detector that detects triaxial acceleration applied to the housing; an integrator that integrates a temporal change of acceleration in each axis which acceleration is detected by the detector; a normalization processor that normalizes an integration value of the acceleration in each axis which value is by the integrator; and a determiner that classifies the numeric value of each axis, which value is normalized by the normalization processor, by a first threshold and determines an impact part on the housing on the basis of a result of the classification for each axis.

20 Claims, 13 Drawing Sheets

| G_RXn | G_RYn | G_RZn | IMPACT PART |
|---|---|---|---|
| 1 | 0 | * | SIDE a |
| −1 | 0 | * | SIDE c |
| 0 | 1 | * | SIDE d |
| 0 | −1 | * | SIDE b |
| 1 | 1 | * | CORNER A |
| 1 | −1 | * | CORNER B |
| −1 | 1 | * | CORNER D |
| −1 | −1 | * | CORNER C |
| 0 | 0 | 1 | EXPOSED SURFACE |
| 0 | 0 | −1 | UNEXPOSED SURFACE |

RADIOGRAPHY IMAGE PHOTOGRAPHING DEVICE AND RADIOGRAPHY IMAGE PHOTOGRAPHING SYSTEM

CROSS REFERENCE TO RELATED APPLICATION

The present invention claims priority under 35 U.S.C § 119 to Japanese Application No. 2016-235248 filed Dec. 2, 2016, the entire content of which is incorporated herein by reference.

BACKGROUND

Technological Field

The present invention relates to a radiography image photographing device and a radiography image photographing system.

Description of the Related Art

In a related art, a computed radiography (CR) cassette including a photostimulable phosphor sheet that accumulates energy of a radiation transmitted through a subject is widely used as a device used in radiography image photographing for a disease diagnosis, and the like.

Recently, a radiography image photographing device (flat panel detector) (also referred to as semiconductor image sensor, and the like) in which a plurality of radiation detection elements is arrayed two-dimensionally (in matrix) and which generates a charge according to a dose of a radiation emitted through a subject and reads the generated charge as a signal value in each of the radiation detection elements is developed as a device replacing the CR cassette. Also, a transportable radiography image photographing device (also referred to as FPD cassette, and the like) in which a sensor panel with a plurality of radiation detection elements being arrayed is housed in a housing is developed.

Since such a transportable radiography image photographing device is highly portable, photographing can be performed in various usage modes. However, there is a case where large impact is received from the outside due to a fall in handling, or the like. This impact from the outside has a bad influence on a sensor substrate housed inside a housing of a transportable radiography image photographing device.

Thus, in a radiography image photographing device in a related art, a triaxial acceleration sensor is provided inside a housing and a part of the housing to which part impact is applied is determined from the magnitude of acceleration detected with respect to each axis (see, for example, JP 2016-1128 A).

However, since determining an impact part from the instantaneous magnitude of detected acceleration of three axes, the radiography image photographing device in the related art cannot identify a phenomenon in detail which phenomenon is, for example, a case where large acceleration is generated instantaneously, or a case where acceleration subsequently varies greatly. Thus, there is a problem that accuracy of determining a part to which impact is applied becomes low.

SUMMARY

The present invention has been made in view of the forgoing problem, and an object of the present invention is to improve accuracy of determining a part to which impact is applied.

To achieve the abovementioned object, according to an aspect of the present invention, a radiography image photographing device reflecting one aspect of the present invention comprises:

a sensor panel in which a plurality of radiation detection elements is arrayed two-dimensionally;

a housing that houses the sensor panel;

a detector that detects triaxial acceleration applied to the housing;

an integrator that integrates a temporal change of acceleration in each axis which acceleration is detected by the detector;

a normalization processor that normalizes an integration value of the acceleration in each axis which value is by the integrator; and a determiner that classifies the numeric value of each axis, which value is normalized by the normalization processor, by a first threshold and determines an impact part on the housing on the basis of a result of the classification for each axis.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention:

FIG. 9A is a view for describing a falling state of a side a;

DETAILED DESCRIPTION OF EMBODIMENTS

Hereinafter, a transportable radiography image photographing device according to an embodiment of the present invention will be described with reference to the drawings. However, the scope of the invention is not limited to the disclosed embodiments.

Note that there is a case where a transportable radiography image photographing device is simply referred to as a radiography image photographing device in the following. Also, in the following, a so-called indirect-type radiography image photographing device that includes a scintillator or the like and that acquires an electric signal by converting an emitted radiation into an electromagnetic wave, which has a different wavelength, such as visible light will be described as a radiography image photographing device. However, an embodiment of the present invention can be also applied to a so-called direct-type radiography image photographing device that directly detects a radiation with a radiation detection element without a scintillator or the like.

[Circuit Configuration and the Like of Radiography Image Photographing Device]

Figure 1:
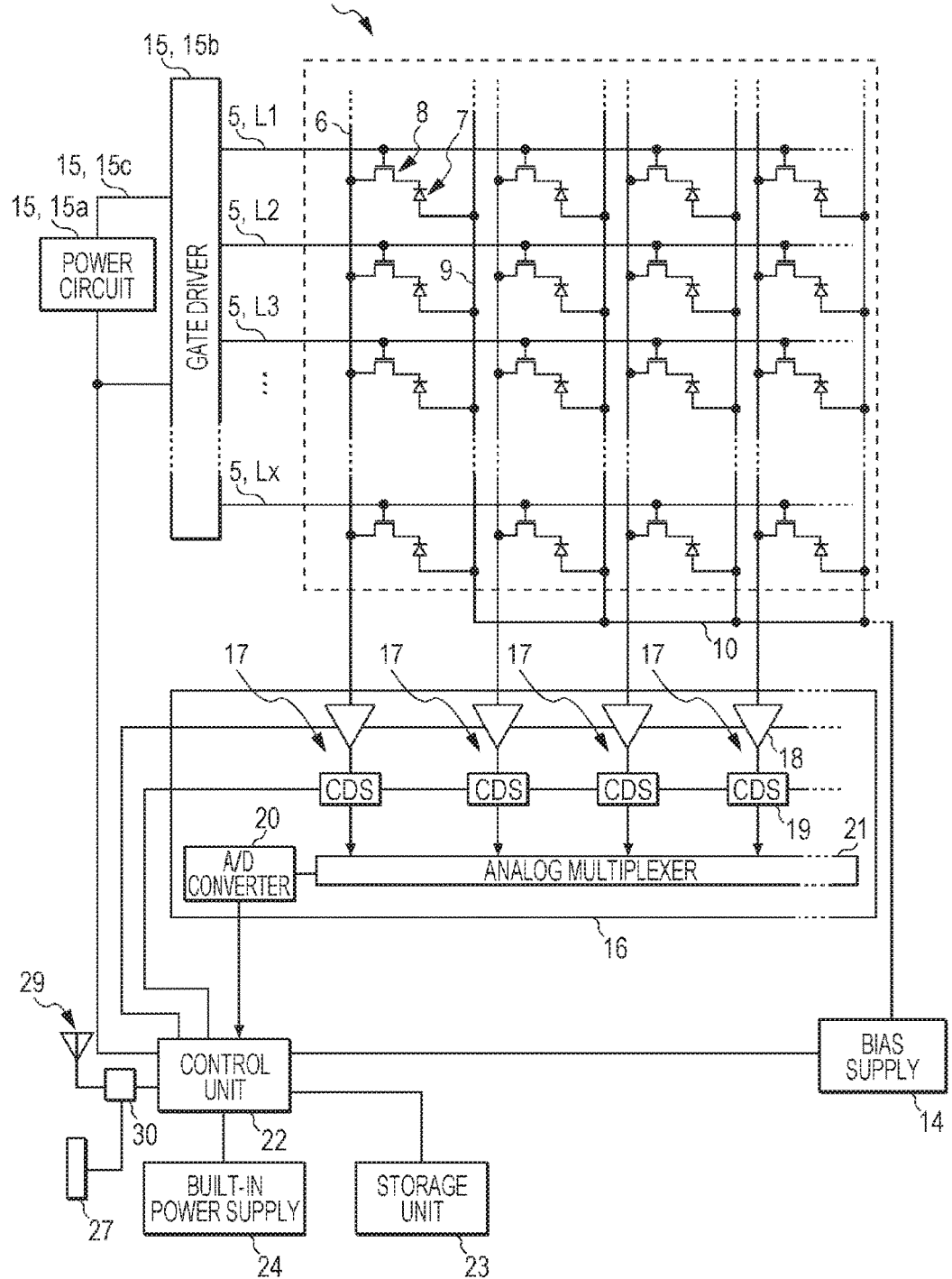
FIG. 1 is a block diagram illustrating an equivalent circuit of a transportable radiography image photographing device according to an embodiment of the present invention.

First, a circuit configuration and the like of a radiography image photographing device according to the present embodiment will be described. FIG. 1 is a block diagram illustrating an equivalent circuit of a radiography image photographing device according to the present embodiment. As illustrated in FIG. 1, a plurality of radiation detection elements 7 is arrayed two-dimensionally (in matrix) on a sensor substrate 51 described later (see FIG. 2 described later) in a radiography image photographing device 1.

Then, a bias line 9 is connected to each radiation detection element 7, a reverse bias voltage being applied thereto by a bias supply 14 via the bias line 9 and a connecting line 10 thereof. Also, a thin film transistor (TFT) 8 is connected as a switch element to each radiation detection element 7. The TFT 8 is connected to a signal line 6.

Also, in a scan driving unit 15, an on-state voltage and an off-state voltage supplied by a power circuit 15a via a wiring line 15c are switched by a gate driver 15b and are applied to each of lines L1 to Lx of scanning lines 5. When the off-state voltage is applied via the scanning lines 5, the TFTs 8 become an off-state, break conduction between the radiation detection elements 7 and the signal lines 6, and accumulate charges in the radiation detection elements 7. Also, when the on-state voltage is applied via the scanning lines 5, the TFTs 8 become an on-state and release, to the signal lines 6, the charges accumulated in the radiation detection elements 7.

The signal lines 6 are respectively connected to readout circuits 17 in a readout IC 16. When the on-state voltage is applied by the gate driver 15b to a line L of the scanning lines 5 in processing of reading a signal value D, a TFT 8 becomes an on-state, a charge flows from a radiation detection element 7 into a readout circuit 17 via the TFT 8 and a signal line 6, and a voltage value corresponding to an amount of the flowing charge is output from an amplifier circuit 18.

A correlated double sampling circuit (described as "CDS" in FIG. 1) 19 reads and outputs a voltage value, which is output from an amplifier circuit 18, as a signal value D of an analog value. In such a manner, in the present embodiment, the readout circuits 17 of the readout IC 16 read, as signal values D, charges that are generated in the radiation detection elements 7 according to a dose of an emitted radiation.

Then, signal values D output from amplifier circuits 18 are serially transmitted to an A/D converter 20 via an analog multiplexer 21, are serially converted into signal values D of digital values in the A/D converter 20, and are serially stored or held in a storage unit 23. In the present embodiment, the reading processing is performed while the on-state voltage is serially applied by the gate driver 15b of the scan driving unit 15 to the lines L1 to Lx of the scanning lines 5, whereby signal values D are read from all of the radiation detection elements 7.

A control unit 22 includes a computer, a field programmable gate array (FPGA), or the like in which a central processing unit (CPU), a read only memory (ROM), a random access memory (RAM), an input/output interface, and the like (not illustrated) are connected to a bus. Note that a special control circuit may be included.

A storage unit 23 including a static RAM (SRAM), a synchronous DRAM (SDRAM), a NAND-type flash memory, or the like, and a built-in power supply 24 including a lithium ion capacitor are connected to the control unit 22. Also, a communicator 30 to communicate with the outside in a wireless system or a wired system via an antenna 29 or a connector 27 is connected to the control unit 22.

Also, the control unit 22 (technically speaking, TFT control circuit 221 described later) performs control such as controlling application of a reverse bias voltage from the bias supply 14 to each radiation detection element 7, making the scan driving unit 15, the readout circuit 17, and the like perform processing of reading a signal value D from the radiation detection element 7 by controlling operations thereof, storing or holding the read signal value D in the storage unit 23, or transferring the stored or held signal value D to the outside via the communicator 30 in the above-described manner.

[Configuration or the Like of Transportable Radiography Image Photographing Device]

Figure 2:
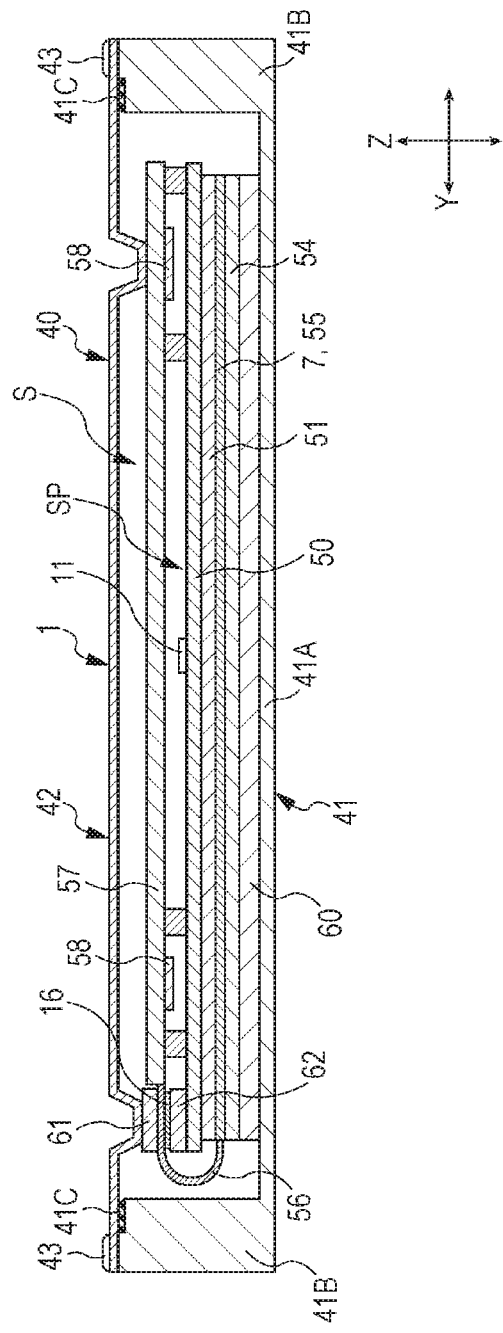
FIG. 2 is a sectional view illustrating a configuration of the transportable radiography image photographing device according to the embodiment of the present invention.

FIG. 2 is a sectional view illustrating a configuration of the transportable radiography image photographing device according to the present embodiment. As illustrated in FIG. 2, a sensor panel SP (also referred to as TFT panel and the like) is housed in a housing 40 in the radiography image photographing device 1. Note that in FIG. 2, the radiography image photographing device 1 is illustrated in such a manner that a radiation incident surface (also referred to as exposed surface) 41A to which a radiation is emitted is arranged on a lower side in the drawing. Also, in the following, a vertical direction in the radiography image photographing device 1 will be described on the basis of a case where the radiography image photographing device 1 is arranged in the state in FIG. 2.

In the present embodiment, the housing 40 of the radiography image photographing device 1 mainly includes a front plate 41 including a substantially rectangle-tabular radiation incident surface 41A and a side wall 41B vertically provided in an outer periphery thereof, and a substantially tabular back plate 42. In the present embodiment, for example, the front plate 41 is made of fiber reinforced plastic and the back plate 42 is made of metal.

Also, the back plate 42 is attached to the side wall 41B of the front plate 41 by a screw 43 that is an engaging member. The back plate 42 has a box shape in combination with the front plate 41.

A packing 41C is inserted between the back plate 42 and the front plate 41, and air-tightness or water-tightness inside the housing 40 is secured.

In the present embodiment, a sensor panel SP is formed in the following manner. Note that in the following, a surface of each substrate or the like which surface is on a side of facing the front plate 41 (that is, surface on lower side in drawing) is referred to as a front surface, and a surface on a side of facing the back plate 42 (that is, surface on upper side in drawing) is referred to as a rear surface. Also, each of the housing 40, the front plate 41, the back plate 42, the sensor panel SP, a base 50, substrates 51 and 54 described later, a scintillator 55, and a PCB substrate 57 is rectangular when seen in a radiation incident direction, and is arranged in such a manner that each of long sides and short sides are in parallel. Then, in the following, a description will be made with a direction along a short side of the housing 40 as an X-axis direction, a direction along a long side thereof as a Y-axis direction, and a direction orthogonal to the X-axis direction and the Y-axis direction (incident direction of radiation) as a Z-axis direction.

The sensor panel SP includes a base 50 including a metal layer (not illustrated) such as lead that shields against radiation. A sensor substrate 51 including a glass substrate or the like is arranged on a front surface side of the base 50. The above-described plurality of radiation detection elements 7, and the like are arranged two-dimensionally on a front surface of the sensor substrate 51.

Also, a scintillator 55 is formed on a surface on one side of a scintillator substrate 54 including a glass substrate or the like. In the present embodiment, the sensor substrate 51 and the scintillator substrate 54 are arranged in such a manner that the scintillator 55 and each radiation detection element 7 face each other. The sensor substrate 51 and the scintillator substrate 54 are pasted to each other by an adhesive (not illustrated) in a part outside the radiation detection elements 7, the scintillator 55, and the like.

The signal lines 6 (see FIG. 1) and the like wired on the sensor substrate 51 are connected to a flexible circuit substrate 56 in which a chip such as the readout IC 16 is mounted on a film. The flexible circuit substrate 56 is routed to a rear surface side of the base 50 and is connected to the PCB substrate 57 or the like that is included as a circuit substrate.

A circuit such as the above-described control unit 22, storage unit 23, or the like (see FIG. 1), an electronic member, and the like (hereinafter, integrally referred to as electronic device 58) are arranged on the PCB substrate 57. Note that the electronic device 58 may be arranged on a rear surface side (or both of front surface side and rear surface side) of the PCB substrate 57, although a state in which the electronic device 58 is arranged on a front surface side of the PCB substrate 57 is illustrated in FIG. 2.

In the radiography image photographing device 1 according to the present embodiment, the sensor panel SP is formed in the above manner. Since the electronic device 58 is arranged on the rear surface side, that is, a side of the back plate 42 of the sensor panel SP, it is possible to access the electronic device 58 only by removing the back plate 42 (that is, without taking sensor panel SP out of housing 40) and to easily perform replacement of the electronic device 58, or the like.

Also, as illustrated in FIG. 2, a spacer 60 is arranged between the scintillator substrate 54 and the front plate 41. Also, in the present embodiment, a heat conducting member 61 is arranged between the readout IC 16 and the back plate 42. Heat generated in the readout IC 16 is conducted to the side of the back plate 42 and is released from the back plate 42 to the outside of the device. Also, a heat insulating member 62 is arranged between the readout IC 16 and the base 50 of the sensor panel SP. The heat generated in the readout IC 16 is prevented from being transmitted to a side of the sensor panel SP.

Figure 3:
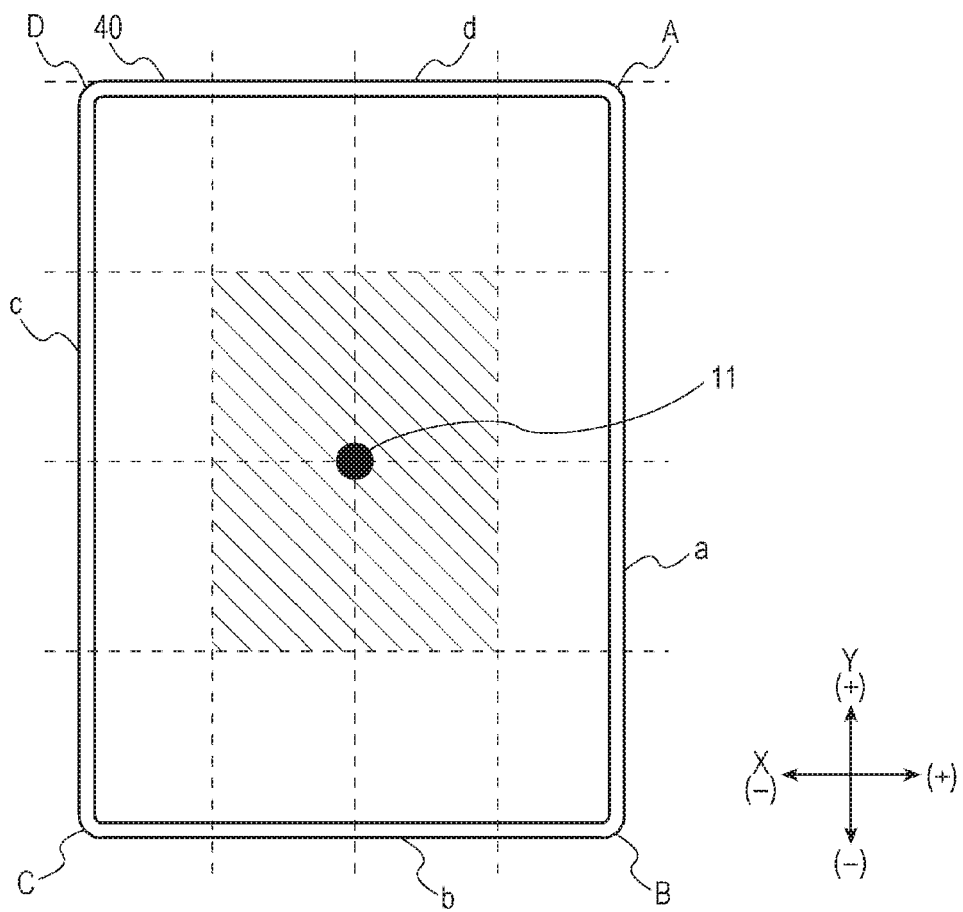
FIG. 3 is a view for describing a state in which a strain sensor is arranged at a center in an X-axis direction and a Y-axis direction of the radiography image photographing device.

Also, as illustrated in FIG. 2 and FIG. 3, when the housing 40 of the radiography image photographing device 1 is seen in the incident direction of a radiation, an acceleration sensor 11 as a detector is provided at a center part thereof. In a case where the housing 40 is seen in the incident direction of a radiation and a plane surface thereof is equally divided into 16 pieces by 4×4, this acceleration sensor 11 is preferably arranged in four center regions and is more preferably in a position that is a center in each of the X-axis direction and the Y-axis direction. This attachment position of the acceleration sensor 11 substantially matches a barycentric position of the radiography image photographing device 1. Also, a barycentric position of the whole radiography image photographing device 1 may be calculated and the acceleration sensor 11 may be attached to the barycentric position.

Also, although being attached to the back surface side of the base 50, the acceleration sensor 11 may be equipped in a different place such as a wall of the housing 40.

[Control System of Radiography Image Photographing Device]

Figure 4:
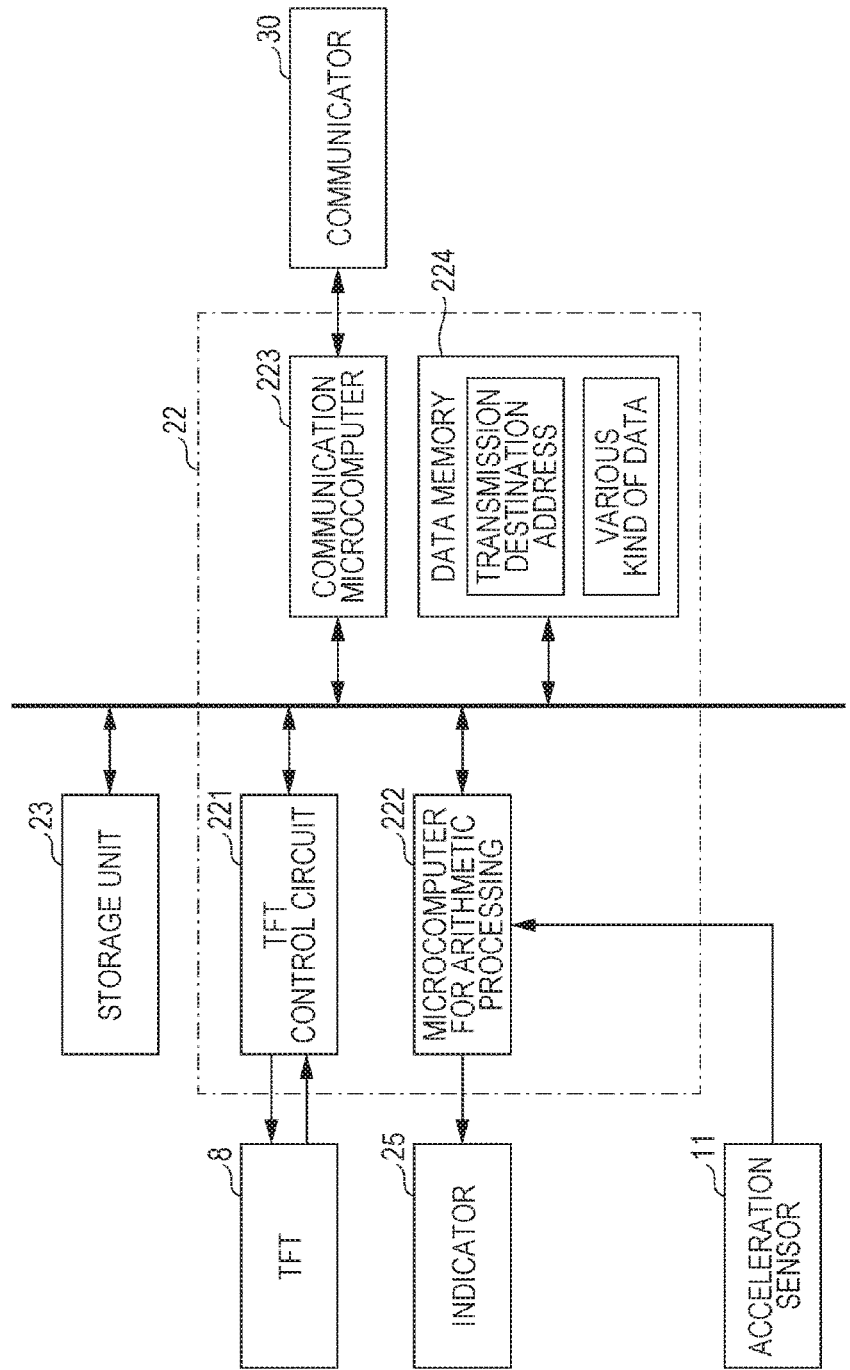
FIG. 4 is a block diagram illustrating a control system of the radiography image photographing device.

FIG. 4 is a block diagram illustrating a control system of the radiography image photographing device 1.

As illustrated in the drawing, the radiography image photographing device 1 includes a TFT control circuit 221 that controls the TFTs 8 respectively connected to the radiation detection elements 7, a microcomputer for arithmetic processing 222 that performs processing of calculating an impact part on the basis of acceleration detected by the acceleration sensor of the radiography image photographing device 1, a communication microcomputer 223 that controls the communicator 30 that communicates with the outside of the radiography image photographing device 1, a data memory 224 that is a non-volatile memory storing various kinds of data, and a communication bus connecting these. These form the above-described control unit 22.

Note that the above-described scan driving unit 15 and readout IC 16 are not illustrated in FIG. 4.

The TFT control circuit 221 includes, for example, a field programmable gate array (FPGA) and a function thereof is as described above.

The communication microcomputer 223 controls the communicator 30 and performs transmission/reception of data or a command with respect to an external device other than the radiography image photographing device 1. Also, it is possible to transmit and receive predetermined data or a predetermined command while specifying a transmission/reception destination.

The acceleration sensor 11 can individually detect acceleration in three directions that are the X-axis direction, the Y-axis direction, and the Z-axis direction of the housing 40 and can output the acceleration to the microcomputer for arithmetic processing 222.

Note that the acceleration sensor 11 only needs to be able to detect acceleration of at least three axes and is not limited to what has the above function. For example, an acceleration sensor 11 may only have a function of detecting and outputting acceleration signals of three axes and a side of the control unit 22 may have a configuration of acquiring determination whether the acceleration is equal to or larger than a threshold, or acceleration before and after the determination.

Figure 5:
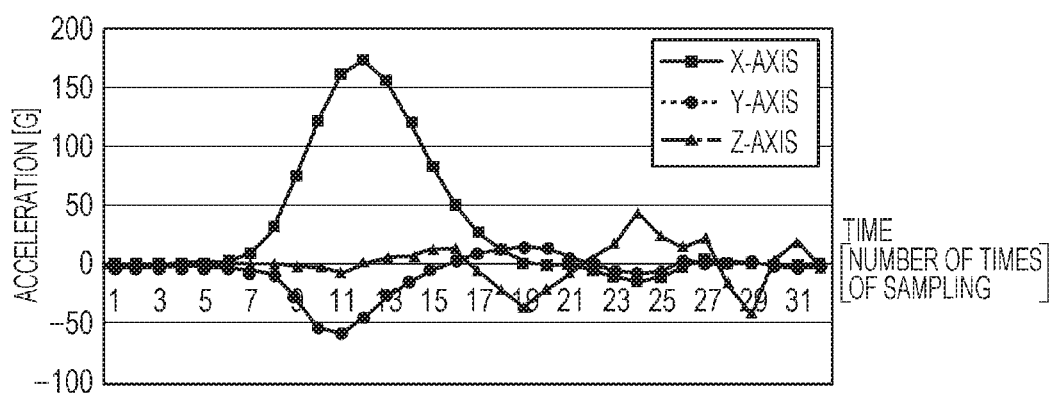
FIG. 5 is a diagram illustrating detected acceleration input from an acceleration sensor into a microcomputer for arithmetic processing.

In FIG. 5, detected acceleration input into the microcomputer for arithmetic processing 222 by the acceleration sensor 11 is illustrated.

More specifically, when acceleration exceeding an output threshold is detected with respect to any of the three axes, 32 pieces of detected acceleration before and after the moment, detected acceleration at the moment being included, of all of the three axes are input into the microcomputer for arithmetic processing 222.

Note that the total number of pieces of output detected acceleration before and after the moment is just an example and can be arbitrarily changed. However, at least a plurality of pieces needs to be output.

The microcomputer for arithmetic processing 222 is connected to the acceleration sensor 11 via an amplifier, an A/D converter, and the like (not illustrated), and acceleration detected by the acceleration sensor 11 is input thereto.

Also, the microcomputer for arithmetic processing 222 stores a program for executing various kinds of processing related to acceleration generated in each part of the radiography image photographing device 1 due to impact from the outside, and executes each kind of processing based on this.

In the following, various kinds of processing performed by the microcomputer for arithmetic processing 222 will be described.

[Impact Part Detection Processing]

When acceleration of the three axes which acceleration is detected by the acceleration sensor 11 is input, the microcomputer for arithmetic processing 222 executes impact part detection processing of determining a part, to which impact is applied, on the housing 40 of the radiography image photographing device 1. In this impact part detection processing, a part that may crash with a floor in falling of the radiography image photographing device 1 is an object of determination. More specifically, to which of ten parts impact due to a crash is applied is determined, the ten parts being four corners A to D and four sides a to d of the housing 40, and a radiation incident surface (exposed surface) and a back surface (unexposed surface) of the housing 40.

Figure 14:
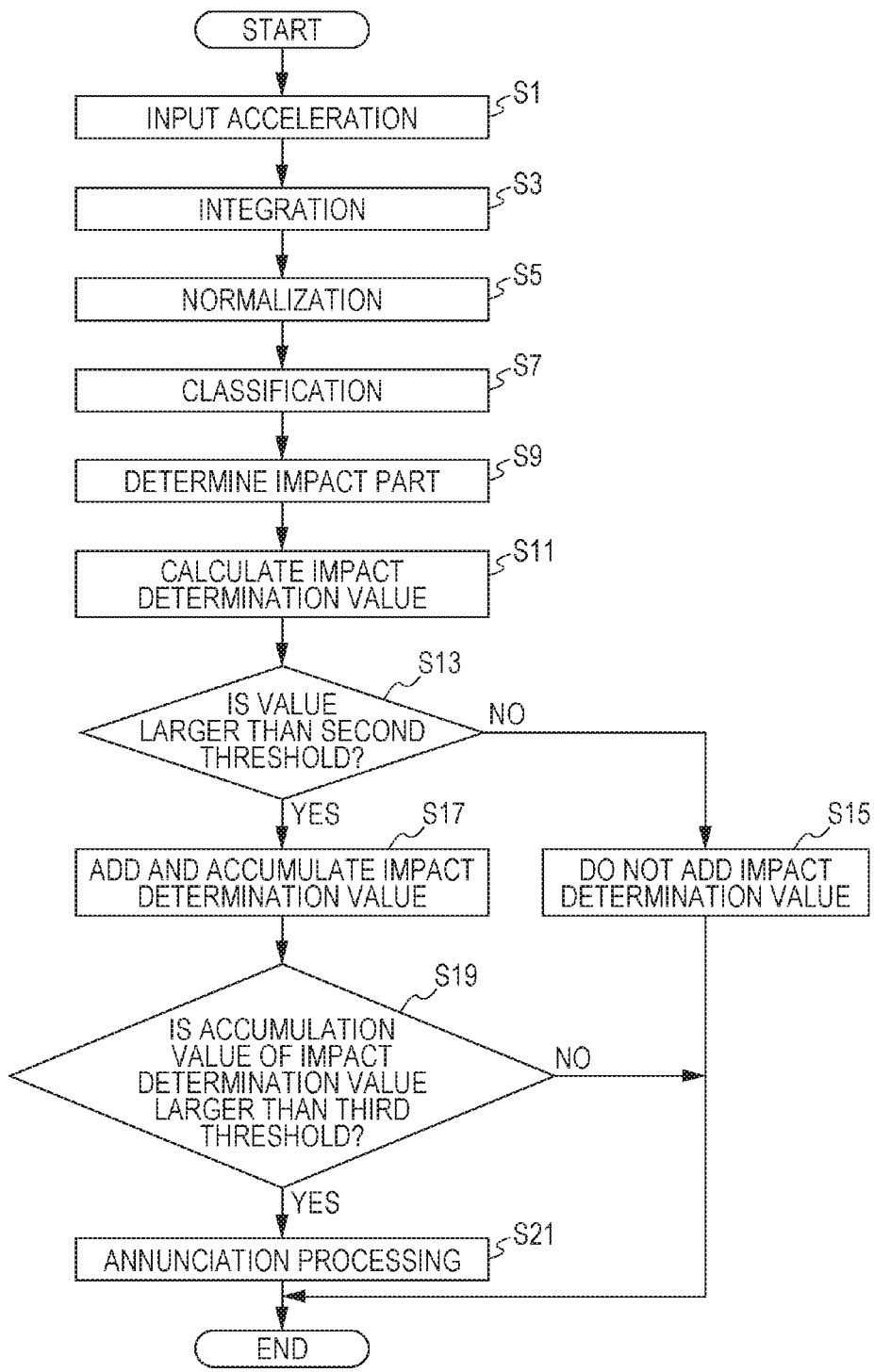
FIG. 14 is a flowchart in which impact part detection processing and impact history accumulation processing are successively executed.

FIG. 14 is a flowchart in which the impact part detection processing and impact history accumulation processing described later are successively executed. First, the impact part detection processing will be described with reference to FIG. 14.

In the impact part detection processing, when detected acceleration of the three axes is input by the acceleration sensor 11 (see FIG. 5, step S1 in FIG. 14), the microcomputer for arithmetic processing 222 integrates 32 pieces of temporally-changed acceleration of each axis and calculates integration values X, Y, and Z of the axes by the following equations (1) to (3) (step S3 in FIG. 14). Note that these integration values reflect, as polarities, a positive direction (+) and a negative direction (−) determined in the acceleration sensor 11 with respect to the X-axis, Y-axis, and Z-axis.

For example, in a case where acceleration in the negative direction in the X-axis is detected as a whole, an integration value X becomes (−).

By performing these operations, the microcomputer for arithmetic processing 222 functions as an "integrator that integrates a temporal change of acceleration in each axis."

[Mathematical Formula 1]

$$X\text{-axis integration value } X = \sum_{k=1}^{32} x_k \qquad (1)$$

$$Y\text{-axis integration value } Y = \sum_{k=1}^{32} y_k \qquad (2)$$

$$Z\text{-axis integration value } Z = \sum_{k=1}^{32} z_k \qquad (3)$$

Note that integration is not limited to the above method and may be a different method. For example, an integration value only of values in a positive direction of detected acceleration and an integration value only in the negative direction may be calculated with respect to each of the X, Y, and Z axes, and values with larger absolute values may be respectively used as integration values X, Y, and Z.

Next, with a value with the largest absolute value among the integration values X, Y, and Z as max, the microcomputer for arithmetic processing 222 performs normalization of the integration values X, Y, and Z by dividing each of the integration values X, Y, and Z by the absolute value of max, and calculates proportion values Rx, Ry, and Rz of the axes by the following equations (4) to (6) (step S5 in FIG. 14).

By performing these operations, the microcomputer for arithmetic processing 222 functions as a "normalization processor that normalizes an integration value of acceleration in each axis."

$$Rx = X/|\max| \qquad (4)$$

$$Ry = Y/|\max| \qquad (5)$$

$$Rz = Z/|\max| \qquad (6)$$

Figure 6:
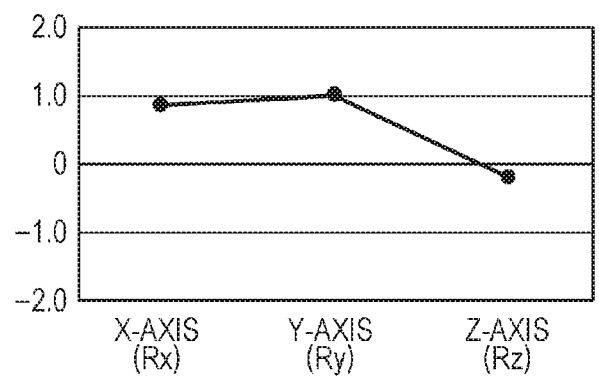
FIG. 6 is a diagram illustrating a proportion value in each of X, Y, and Z axes.

FIG. 6 is a diagram illustrating proportion values Rx, Ry, and Rz of the axes. As illustrated in the drawing, all of these values are in a range of ±1.

A combination of numeric values of the above-described proportion values Rx, Ry, and Rz of the axes has a correspondence relationship with an impact part on the housing 40.

Figure 7A:
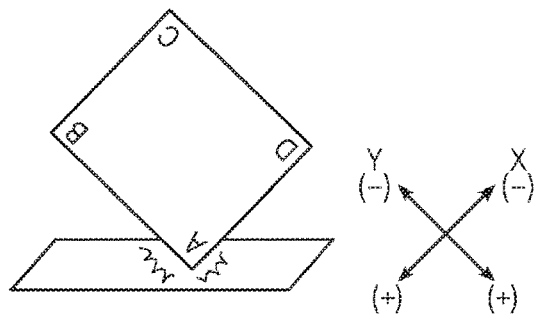
FIG. 7A is a view for describing a falling state of a corner A.
Figure 8:
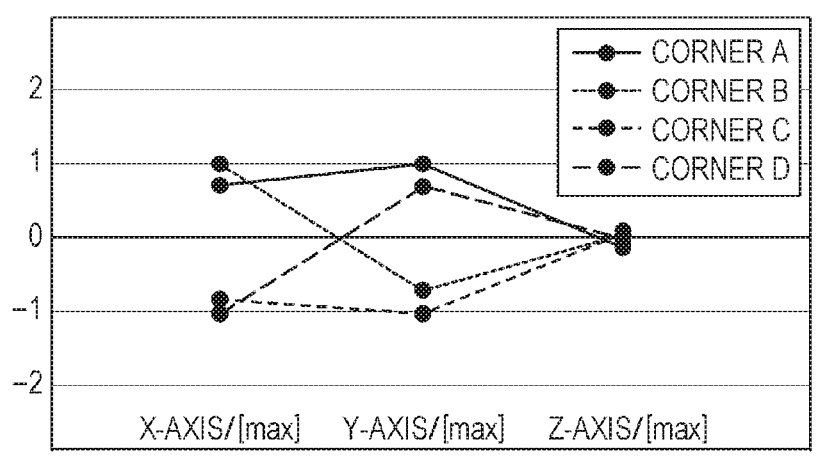
FIG. 8 is a diagram illustrating proportion values in falling at the corners A to D.

As illustrated in FIG. 7A, in a case where a corner A placed on a (+) side in the X-axis direction and a (+) side in the Y-axis direction crashes in a fall, Rx, Ry, and Rz are around 1, 1, and 0 as indicated by values in a diagram of the corner A in FIG. 8.

Figure 7B:
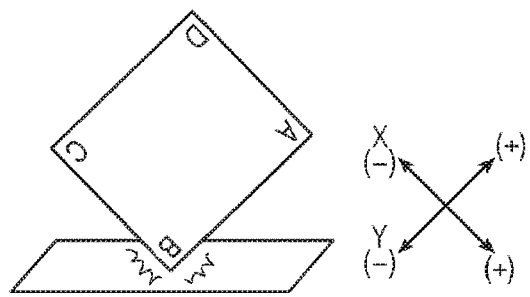
FIG. 7B is a view for describing a falling state of a corner B.

As illustrated in FIG. 7B, in a case where a corner B placed on the (+) side in the X-axis direction and a (−) side in the Y-axis direction crashes in a fall, Rx, Ry, and Rz are around 1, −1, and 0 as indicated by values in a diagram of the corner B in FIG. 8.

Figure 7C:
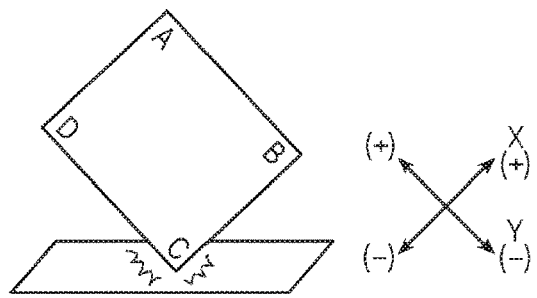
FIG. 7C is a view for describing a falling state of a corner C.

As illustrated in FIG. 7C, in a case where a corner C placed on a (−) side in the X-axis direction and the (−) side in the Y-axis direction crashes in a fall, Rx, Ry, and Rz are around −1, −1, and 0 as indicated by values in a diagram of the corner C in FIG. 8.

Figure 7D:
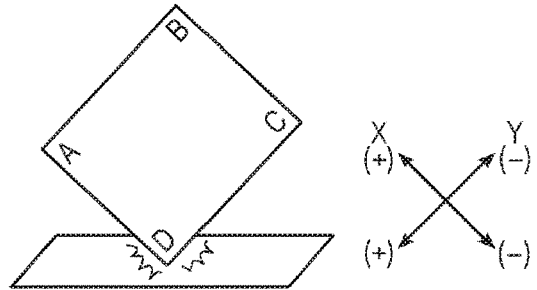
FIG. 7D is a view for describing a falling state of a corner D.

As illustrated in FIG. 7D, in a case where a corner D placed on the (−) side in the X-axis direction and the (+) side in the Y-axis direction crashes in a fall, Rx, Ry, and Rz are around −1, 1, and 0 as indicated by values in a diagram of the corner D in FIG. 8.

Figure 9A:
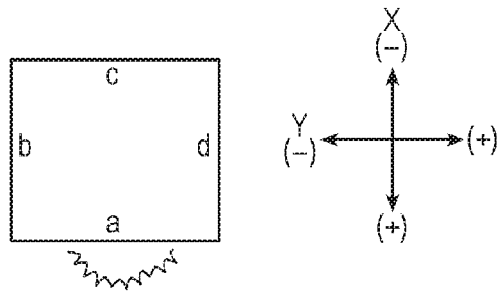
Figures 10, 11:
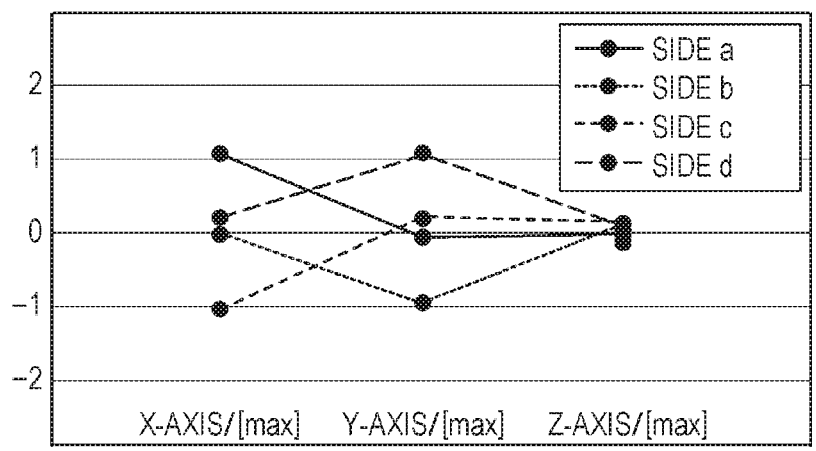
FIG. 10 is a diagram illustrating proportion values in falling at the sides a to d.
FIG. 11 is a chart illustrating a relationship between classification values and ten impact parts.

As illustrated in FIG. 9A, in a case where a whole side a placed on the (+) side in the X-axis direction crashes in a fall, Rx, Ry, and Rz are around 1, 0, and 0 as indicated by values in a diagram of the side a in FIG. 10.

Figure 9B:
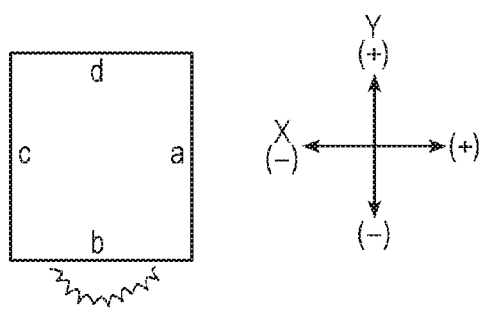
FIG. 9B is a view for describing a falling state of a side b.

As illustrated in FIG. 9B, in a case where a whole side b placed on the (−) side in the Y-axis direction crashes in a fall, Rx, Ry, and Rz are around 0, −1, and 0 as indicated by values in a diagram of the side b in FIG. 10.

Figure 9C:
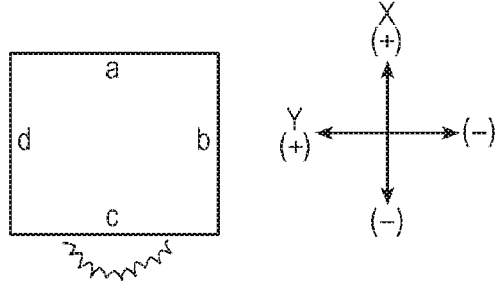
FIG. 9C is a view for describing a falling state of a side c.

As illustrated in FIG. 9C, in a case where a whole side c placed on the (−) side in the X-axis direction crashes in a fall, Rx, Ry, and Rz are around −1, 0, and 0 as indicated by values in a diagram of the side c in FIG. 10.

Figure 9D:
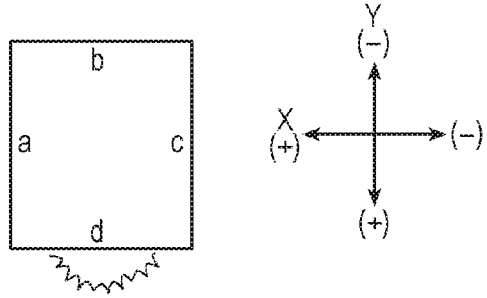
FIG. 9D is a view for describing a falling state of a side d.

As illustrated in FIG. 9D, in a case where a whole side d placed on the (+) side in the Y-axis direction crashes in a fall, Rx, Ry, and Rz are around 0, 1, and 0 as indicated by values in a diagram of the side d in FIG. 10.

Also, in a case where a fall is caused with the radiation incident surface 41A of the housing 40 being in a horizontal state and the whole surface crashes, Rx and Ry are around 0 and only Rz is around 1.

Also, in a case where a fall is caused with a rear surface of the back plate 42 of the housing 40 being in a horizontal state and the whole surface crashes, Rx and Ry are around 0 and only Rz is around −1.

That is, classification is as follows.

If $Rx \leq -jx$, $G_{RXn}=-1$. If $-jx<Rx<jx$, $G_{RXn}=0$. If $jx \leq Rx$, $G_{RXn}=1$.

If $Ry \leq -jy$, $G_{RYn}=-1$. If $-jy<Ry<jy$, $G_{RYn}=0$. If $jy \leq Ry$, $G_{Ryn}=1$.

If $Rz \leq -jz$, $G_{RZn}=-1$. If $-jz<Rz<jz$, $G_{RZn}=0$. If $jz \leq Rz$, $G_{RZn}=1$.

Note that each of first thresholds jx, jy, and jz is preferably 0.41 or smaller and is more preferably 0.3 or smaller. However, 0.05 is a lower limit. Also, different numeric values may be respectively set with respect to the first thresholds jx, jy, and jz. An input unit may be provided in the control unit 22, and it may be made possible to arbitrarily and individually set and input each of the first thresholds jx, jy, and jz.

Note that in a case where falling at the corners A to D or falling at the sides a to d is caused, at least one of $G_{RXn}$ and $G_{RYn}$ become +1 or −1. Thus, a value of $G_{RZn}$ is not used in determination in such a case, and a value of $G_{RZn}$ is used in determination only in a case of a surface fall in which case both values of $G_{RXn}$ and $G_{RYn}$ become 0.

A relationship between a combination of the classification values $G_{RXn}$, $G_{RYn}$, and $G_{RZn}$ and ten parts to which impact due to a fall is applied and which are the four corners A to D and the four sides a to d of the housing 40, and the radiation incident surface (exposed surface) and the back surface (unexposed surface) of the housing 40 is illustrated in FIG. 11.

Since being indefinite numerals as described above, values of $G_{RZn}$ of the corners A to D and the four sides a to d are expressed by "*" in FIG. 11. In a case of not being 0, $G_{RXn}$ and $G_{RYn}$ are used for determination in priority to $G_{RZn}$. Thus, it is possible to simplify processing while keeping determination accuracy.

The microcomputer for arithmetic processing 222 stores, in the data memory 224, table data indicating a correspondence relationship between a combination of the classification values $G_{RXn}$, $G_{RYn}$, and $G_{RZn}$ and a part to which impact due to a fall is applied which relationship is illustrated in FIG. 11. When the classification values $G_{RXn}$, $G_{RYn}$, and $G_{RZn}$ are calculated from acceleration of the three axes which acceleration is detected by the acceleration sensor 11, the microcomputer for arithmetic processing 222 refers to the table data and specifies a part to which impact is applied (step S9 in FIG. 14).

Accordingly, the microcomputer for arithmetic processing 222 functions as a "determiner that determines an impact part on the housing on the basis of a classification result of each axis."

Figure 12A:
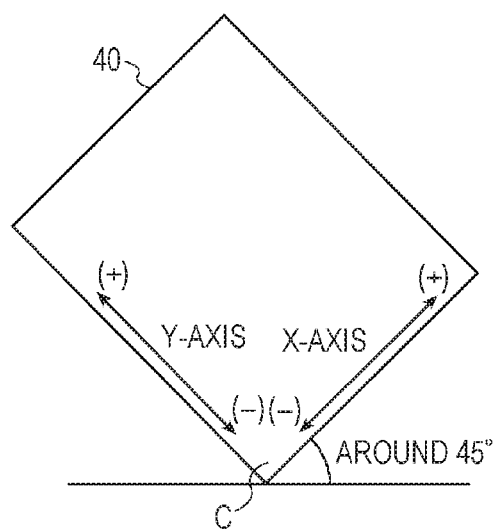
FIG. 12A is a view for describing a position of a housing in an ideal corner fall.
Figure 12B:
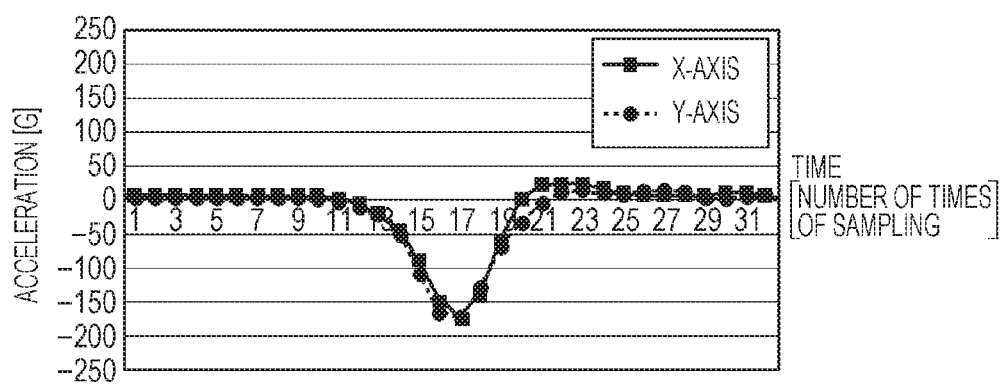
FIG. 12B is a diagram illustrating an output in each of an X-axis and a Y-axis by an acceleration sensor in that case.

Determination accuracy in a case where a corner fall of the housing 40 is caused will be described in detail. A position of the housing 40 in an ideal corner fall is illustrated in FIG. 12A and an output in each of the X-axis and the Y-axis by the acceleration sensor 11 in the case is illustrated in FIG. 12B.

Here, a case where a fall and a crash are from the corner C in a state in which the Z-axis of the housing 40 is horizontal and both of the X-axis and the Y-axis thereof are inclined for 45° is illustrated.

In this case, absolute values of the maximum values of detected acceleration in the X-axis and the Y-axis which acceleration is input by the acceleration sensor 11 into the microcomputer for arithmetic processing 222 substantially match each other. Shapes of a valley also match each other substantially. Thus, magnitude of integration values X and Y is approximate and each of the classification values $G_{RXn}$ and $G_{RYn}$ calculated from the proportion values Rx and Ry is −1. The microcomputer for arithmetic processing 222 determines that a fall is from the corner C.

On the other hand, a radiography image photographing device in a related art makes a determination, without performing integration with respect to an output by an acceleration sensor 11 in each of an X-axis and a Y-axis, only from magnitude thereof.

In FIG. 12B, in outputs in the X-axis and the Y-axis by the acceleration sensor 11 in that case, large acceleration is detected in the negative direction (−) with respect to detected acceleration in the X-axis and the Y-axis. Thus, the radiography image photographing device in the related art can also determine that a fall is from a corner C.

Figure 13A:
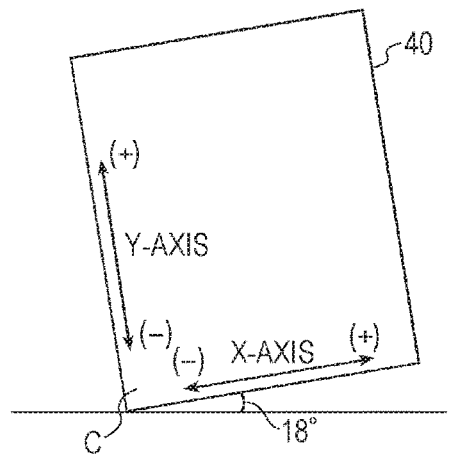
FIG. 13A is a view for describing a position of a housing in a corner fall with which accurate direction is difficult.
Figure 13B:
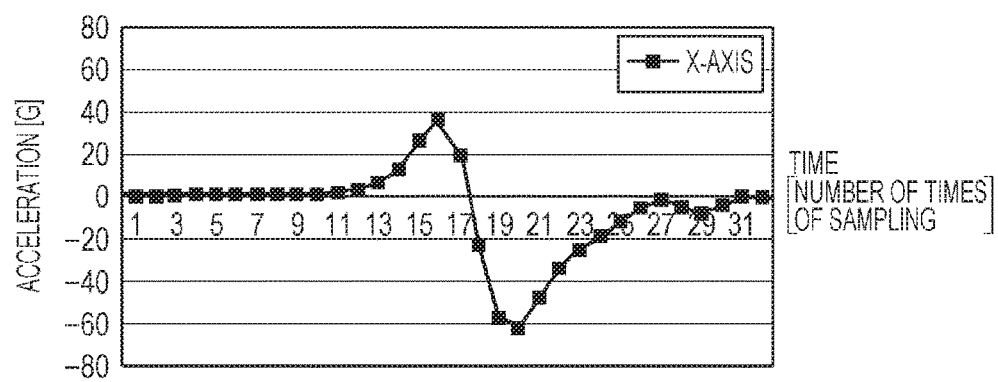
FIG. 13B is a diagram illustrating an output in the X-axis by the acceleration sensor in that case.
Figure 13C:
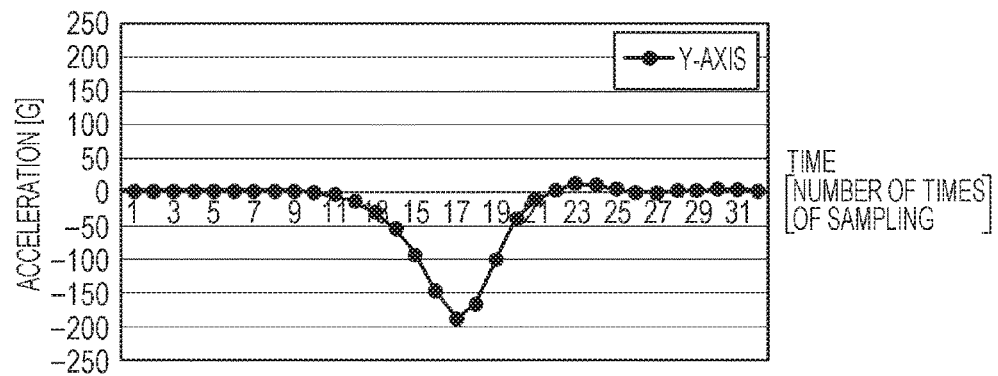
FIG. 13C is a diagram illustrating an output in the Y-axis by the acceleration sensor in that case.

Next, a position of the housing 40 in a corner fall with which accurate detection is difficult is illustrated in FIG. 13A, an output in the X-axis by the acceleration sensor 11 in the case is illustrated in FIG. 13B, and an output in the Y-axis by the acceleration sensor 11 in the case is illustrated in FIG. 13C.

Here, a case where a fall and a crash are from the corner C in a state in which the Z-axis of the housing 40 is horizontal, the X-axis thereof is inclined for 18°, and the Y-axis thereof is inclined for 72° is illustrated.

As described above, when the X-axis becomes close to a horizontal state, a small peak is initially generated in a direction opposite to a radical direction (+ side in this case) and a large peak is subsequently generated in the radical direction (− side in this case) in detected acceleration in the X-axis.

Since a determination is initially made on the basis of acceleration in the opposite direction of the radical direction with respect to the X-axis direction, the radiography image photographing device in the related art makes an erroneous determination that a fall is from a corner B.

On the other hand, in a case of the radiography image photographing device 1, the microcomputer for arithmetic processing 222 integrates a temporal change of detected acceleration in the X-axis. Thus, since large acceleration in a right direction (− side) is subsequently generated even when acceleration is initially generated in the opposite direction (+ side), an integration value of the acceleration indicates the right direction (− side) and it is possible to correctly determine that a fall is from the corner C.

[Impact History Accumulation Processing]

The microcomputer for arithmetic processing 222 calculates an impact determination value for each of the above-described ten impact parts of the housing 40 on the basis of acceleration detection in the three axes by the acceleration sensor 11, and executes impact history accumulation processing of adding up and accumulating the impact determination values.

This impact history accumulation processing is to quantify, add up, and accumulate impacts temporally applied to the ten parts of the housing 40 and is to predict and previously give annunciation of generation of malfunction on the basis of accumulated numeric values (impact determination value).

Note that this impact history accumulation processing is preferable since impact determination values accumulated for each impact part are integrated for each damaged part and accuracy of predicting malfunction is improved, the processing being executed after an impact part is determined in the above-described impact part detection processing.

When detected acceleration in three axes is input by the acceleration sensor 11, the microcomputer for arithmetic processing 222 calculates an impact determination value from these (step S11 in FIG. 14).

The impact determination value is calculated by synthesizing of integration values of absolute values of the above-described 32 pieces of detected acceleration in each of the three axes.

That is, absolute values of 32 pieces of detected acceleration are added up in each of the X-axis, the Y-axis, and the Z-axis. Then, the integration values respectively added up for the three axes in such a manner are synthesized by being added up after being multiplied and weighted respectively by coefficients individually set for the X-axis, the Y-axis, and the Z-axis, whereby an impact determination value is calculated.

A coefficient for weighting in each axis may be individually set for each of the ten parts, which are objects of determination of an impact part, according to likeliness of malfunction. In that case, in calculation of an impact determination value, an impact part calculated by the above-described impact part detection processing is read and a coefficient for weighting in each axis is determined according to this.

Note that various numeric values with which magnitude of impact applied to the ten parts of the housing 40 can be determined can be used as an impact determination value.

For example, a sum value, a synthesized value (weighted sum value), or the like in each axis of absolute values of the maximum values of acceleration detected by the acceleration sensor 11 may be used.

The microcomputer for arithmetic processing 222 determines whether a calculated impact determination value is larger than a predetermined second threshold (step S13 in FIG. 14).

This second threshold may be arbitrarily set and input by an input unit provided in parallel in the control unit 22.

Then, in a case where the impact determination value is not larger than the second threshold, all impact determination values are not recorded and are erased (step S15 in FIG. 14). Then, the processing is ended directly.

On the other hand, in a case of being larger than the second threshold, the impact determination value is added to the data memory 224 and recorded as an accumulation value (step S17 in FIG. 14).

That is, the microcomputer for arithmetic processing 222 individually records, in the data memory 224, an accumulation value of impact determination values for each of the ten parts that are objects of determination of an impact part in the impact part detection processing, and adds a newly-calculated impact determination value to an accumulation value of impact determination values in a specific part, which is determined in last impact part detection processing, among the ten parts.

By calculating an impact determination value and updating an accumulation value thereof in such a manner, the microcomputer for arithmetic processing 222 functions as an "impact history part that adds and accumulates, for each impact part on the housing, an impact determination value based on detection by the detector."

The microcomputer for arithmetic processing 222 determines whether the calculated accumulation value of impact determination values is larger than a predetermined third threshold (step S19 in FIG. 14).

This third threshold is set individually for each of the ten parts that are objects of determination in the impact part detection processing. Also, this value may be arbitrarily set and input by the input unit provided in parallel in the control unit 22.

Then, in a case where the accumulation value of impact determination values is not larger than the predetermined third threshold, the processing is directly ended.

Also, in a case where the accumulation value of impact determination values is larger than the predetermined third threshold, annunciation processing is performed (step S21).

The annunciation processing will be described.

The microcomputer for arithmetic processing 222 is connected to an indicator 25 via an interface (not illustrated). The indicator 25 includes a plurality of LED lamps respectively corresponding to the ten impact parts that are objects of determination in the impact part detection processing. Then, the microcomputer for arithmetic processing 222 performs, as the annunciation processing, operation control of turning on an LED lamp of the indicator 25 which lamp corresponds to an impact part in which an accumulation value becomes larger than the third threshold.

Note that an object of executing the annunciation processing is not limited to the indicator 25. Character information or the like indicating in which impact part an accumulation value of impact determination values is larger than the third threshold may be displayed on a liquid-crystal panel or the like. Alternatively, an annunciation unit by sound may be used.

In addition to the annunciation processing of giving annunciation from the radiography image photographing device 1, the microcomputer for arithmetic processing 222 executes annunciation processing with respect to the outside of the radiography image photographing device 1.

More specifically, the microcomputer for arithmetic processing 222 transmits, via the communicator 30, a command to the communication microcomputer 223 to give annunciation to a transmission destination address, which is annunciation destination information registered in the data memory 224, that an accumulation value of impact determination values with respect to any of the impact parts becomes larger than the third threshold. Also, at that time, identification information such as ID to specify the radiography image photographing device 1 is also transmitted collaterally.

By performing the annunciation processing in such a manner, the microcomputer for arithmetic processing 222 functions as an "annunciation processor that performs annunciation processing in a case where an accumulation value of impact determination values exceeds a third threshold."

[Technical Effect of Embodiments]

As described above, the radiography image photographing device 1 determines an impact part on the housing 40 by integrating acceleration of three axes which acceleration is detected by the acceleration sensor 11 and classifying a normalized value by a first threshold.

Thus, even in a case where detected acceleration at impact is continuously increased and decreased in a short period, such as a case where a corner fall of the housing 40 is caused in a state close to a side fall (see FIG. 13B), an impact part can be identified correctly and accuracy of determining a part, to which impact is applied, on the housing 40 can be improved.

Also, in a case of integrating detected acceleration, the microcomputer for arithmetic processing 222 of the radiography image photographing device 1 integrates a temporal change of (32 pieces of) acceleration in a predetermined certain period. Thus, a period necessary for determining a part to which impact is applied can be moderately divided and a processing period for determination can be shortened and adjusted properly.

Moreover, since a first threshold for classification of a numeric value acquired by normalization of acceleration is set individually for each axis in the radiography image photographing device 1, appropriate adjustment for determination of an impact part can be performed with respect to an influence due to a shape, a structure, weight, a barycentric position, and stiffness of the housing 40, an arrangement of the acceleration sensor 11, a direction of each axis of the acceleration sensor 11, and the like. Thus, it becomes possible to further improve accuracy of determining a part to which impact is applied.

Specifically, by making a first threshold 0.41 or smaller and further making a first threshold 0.3 or smaller, it is possible to further improve accuracy of determining a part to which impact is applied.

Also, since being arranged at a center part of the housing 40, the acceleration sensor 11 can be arranged near a barycentric position of the radiography image photographing device 1. Thus, it is possible to more accurately detect acceleration of each part in each direction of the housing 40 and to further improve accuracy of determining a part to which impact is applied.

Also, since the radiography image photographing device 1 adds and accumulates, for each impact part on the housing 40, an impact determination value based on detection by the acceleration sensor 11, it is possible to determine a temporal influence of impacts on the radiography image photographing device 1 on the basis of an accumulation value of impact determination values at each impact part and to predict generation of malfunction.

Specifically, since a second threshold is set with respect to an impact determination value and the impact determination value is added and accumulated in a case of being larger than the second threshold, it is possible to eliminate impact in an unnecessary level in determination of a temporal influence of impacts and to more accurately predict generation of malfunction.

Also, since the radiography image photographing device 1 performs annunciation processing in a case where an accumulation value of impact determination values of any of the impact parts exceeds a third threshold, it becomes possible to let surrounding people know a result of predicting generation of malfunction and to avoid radiography image photographing in a broken state.

[Radiography Image Photographing System]

Figure 15:
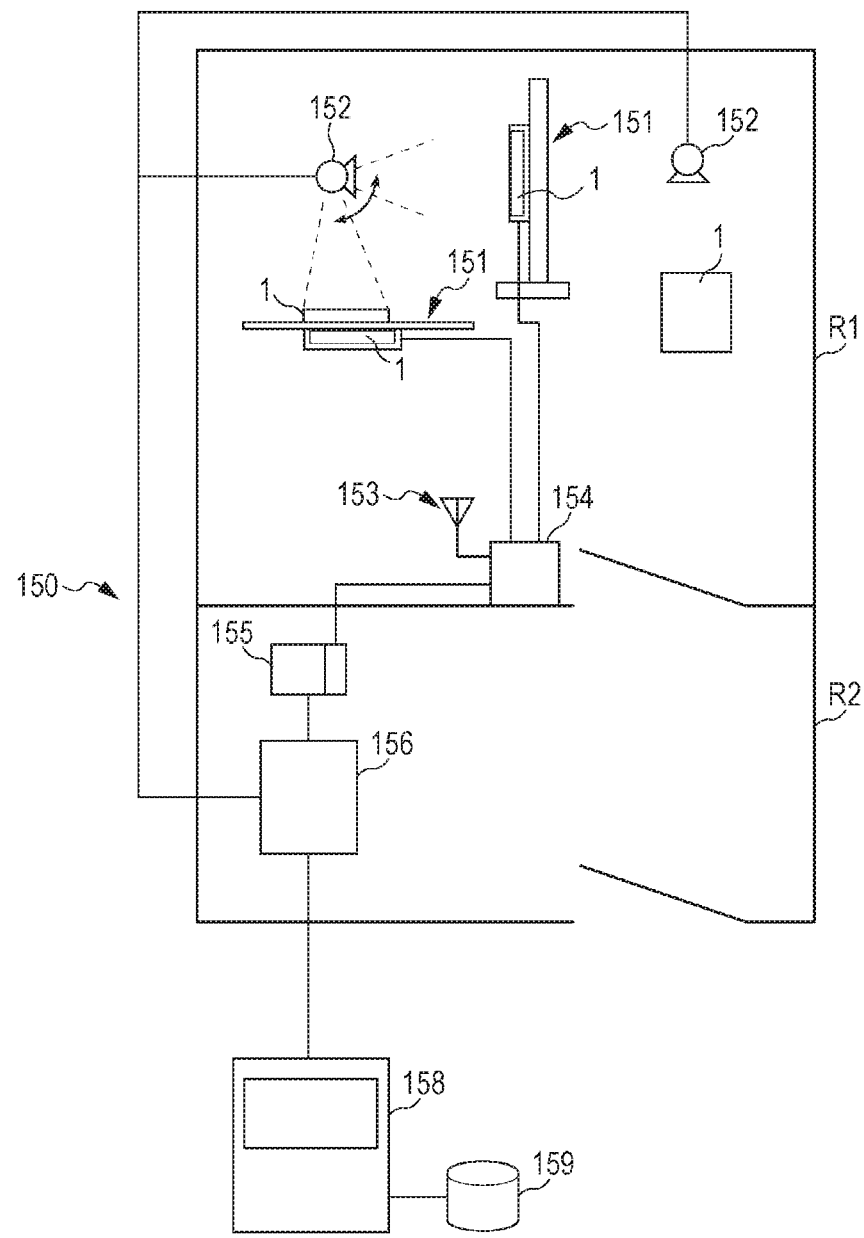
FIG. 15 is a view illustrating a whole configuration of a radiography image photographing system.

Here, a radiography image photographing system in which the above radiography image photographing device 1 is installed will be mentioned. FIG. 15 is a view illustrating a whole configuration of a radiography image photographing system according to the present embodiment. As illustrated in FIG. 15, a radiography image photographing system 150 is arranged, for example, in each of a photographing room R1 in which a radiation is emitted and a subject that is a part of a patient (not illustrated) is photographed, and an anteroom R2 in which an operator such as a radiation technologist performs operation such as emission of a radiation to the subject.

In the present embodiment, a supporting device 151 to which the above-described radiography image photographing device 1 (transportable radiography image photographing device 1) can be loaded, a radiation source 152 that is a radiation generation device including an X-ray tube (not illustrated) that generates a radiation emitted to a subject, a wireless access point (base station) 154 including a radio antenna 153 that relays communication of the radiography image photographing device 1 and a different device in wireless communication thereof, and the like are provided in the photographing room R1.

Also, an operation table 156 of a radiation generation device which table includes an emission start switch 155 or the like to instruct starting of emission of a radiation from the radiation source 152 is provided in the anteroom R2. The operation table 156 is connected to a console 158 that is included as an external processing device provided outside the photographing room.

In the console 158, image processing is performed by utilization of image data, a dark read value, or the like acquired in the radiography image photographing system 150 and generation of a radiation image, and the like are performed. Note that the console 158 can be provided in the anteroom R2. Also, a storage unit 159 including a hard disk or the like is connected to the console 158.

In a case of being installed in the radiography image photographing system 150, the radiography image photographing device 1 can set the console 158 as a destination of annunciation processing to the outside of the radiography image photographing device 1.

More specifically, in execution of annunciation processing, the radiography image photographing device 1 notifies the console 158, via the wireless access point 154 from the communicator 30, of whether an accumulation value of impact determination values with respect to any impact part becomes larger than a third threshold and of identification information of the radiography image photographing device 1.

Moreover, for example, the wireless access point 154 may be connected to an external network such as a wide area network (WAN). Through the network, the radiography image photographing device 1 may transmit, to an information processing terminal or a server in a different area, whether an accumulation value of impact determination values with respect to any impact part becomes larger than a third threshold, and identification information or the like of the radiography image photographing device 1.

In that case, a transmission destination is set as an information processing terminal of an institution that performs maintenance of the radiography image photographing device 1. Thus, a generated condition of an influence of impact on the radiography image photographing device 1 can be recognized instantaneously, and support such as repairing, maintenance, and examination can be made promptly.

Also, a part or all of the functions executed by the microcomputer for arithmetic processing 222 of the radiography image photographing device 1 (function as integrator, normalization processor, determiner, impact history part, and annunciation processor) may be executed by the console 158. In that case, when necessary, a storage unit to store various kinds of data stored by the data memory 224 of the radiography image photographing device 1 may be provided on a side of the console 158.

Also, in that case, data necessary for a function of the integrator, the normalization processor, the determiner, the impact history part, or the annunciation processor executed by the console 158 is transmitted from the communicator 30 of the radiography image photographing device 1. Also, in a case where the console 158 executes a function of a part of any of the integrator, the normalization processor, the determiner, the impact history part, and the annunciation processor, the microcomputer for arithmetic processing 222 of the radiography image photographing device 1 may not have a capacity to execute the function executed by the console 158.

In such a manner, in a case where the console 158 executes a part or all of the functions as the integrator, the normalization processor, the determiner, the impact history part, and the annunciation processor and, for example, in a case where there is a plurality of radiography image photographing devices 1, an amount of generated impact, an accumulation value of impact determination values, a result of predicting generation of malfunction, and the like at an impact part of the radiography image photographing devices 1 can be intensively managed.

Also, a processing burden on the microcomputer for arithmetic processing 222 of the radiography image photographing device 1 can be decreased.

Note that in a case where a part or all of the functions as the integrator, the normalization processor, the determiner, the impact history part, and the annunciation processor are executed outside the radiography image photographing device 1, not only the console 158 but also a configuration in the radiography image photographing system 150 which configuration is a different information processing device that can communicate with the radiography image photographing device 1 (such as a server device that manages data of radiation image) may be used.

[Other]

Note that in the above embodiment, a case where impact history accumulation processing is performed after impact part detection processing on the basis of an impact part determined by the impact part detection processing in the radiography image photographing device 1 has been described as an example.

However, the impact part detection processing and the impact history accumulation processing may not be performed successively.

Also, in execution of the impact history accumulation processing, an impact part may be calculated by a method other than the method in step S1 to S9 in FIG. 14 and the impact history accumulation processing may be performed on the basis of the impact part.

For example, after performing a method of determining an impact part from detected acceleration of three axes without integration which method is similar to that by a radiography image photographing device in a related art, the radiography image photographing device 1 may execute the impact history accumulation processing by the method in step S10 to S21 in FIG. 14 on the basis of the impact part.

Note that a case where the console 158 that belongs to the radiography image photographing system 150 or a different information processing device performs impact part detection processing is in a similar manner.

Although embodiments of the present invention have been described and illustrated in detail, it is clearly understood that the same is by way of illustration and example only and not limitation, the scope of the present invention should be interpreted by terms of the appended claims. Also, it is obvious that the present invention can be arbitrarily modified within the spirit and the scope of the present invention.

What is claimed is:

1. A radiography image photographing device comprising:
    a sensor panel in which a plurality of radiation detection elements is arrayed two-dimensionally;
    a housing that houses the sensor panel;
    a detector that detects triaxial acceleration applied to the housing;
    an integrator that integrates a temporal change of acceleration in each axis which acceleration is detected by the detector;
    a normalization processor that normalizes an integration value of the acceleration in each axis which value is by the integrator; and
    a determiner that classifies the numeric value of each axis, which value is normalized by the normalization processor, by a first threshold and determines an impact part on the housing on the basis of a result of the classification for each axis.

2. The radiography image photographing device according to claim 1, wherein the integrator integrates a temporal change of the acceleration in a predetermined certain period.

3. The radiography image photographing device according to claim 1, wherein the first threshold for classification of the numeric value normalized by the normalization processor is individually determined for each axis.

4. The radiography image photographing device according to claim 1, wherein the first threshold is 0.41 or smaller.

5. The radiography image photographing device according to claim 4, wherein the first threshold is 0.3 or smaller.

6. The radiography image photographing device according to claim 1, wherein the detector is arranged at a center part of the housing when seen in a radiation incident direction.

7. The radiography image photographing device according to claim 1, further comprising an impact history part that adds and accumulates, for each impact part on the housing, an impact determination value based on detection by the detector.

8. The radiography image photographing device according to claim 7, wherein the impact determination value is added and accumulated by the impact history part in a case of being larger than a second threshold.

9. The radiography image photographing device according to claim 7, further comprising an annunciation processor that performs annunciation processing in a case where an accumulation value of the impact determination value, which is added and accumulated by the impact history part, with respect to any impact part exceeds a third threshold.

10. A radiography image photographing device comprising:
- a sensor panel in which a plurality of radiation detection elements is arrayed two-dimensionally;
- a housing that houses the sensor panel;
- a detector that detects impact applied to the housing;
- a determiner that determines an impact part on the housing on the basis of the detection by the detector; and
- an impact history part that adds and accumulates, for each impact part on the housing, an impact determination value based on the detection by the detector.

11. A radiography image photographing system comprising:
- a radiography image photographing device including a sensor panel in which a plurality of radiation detection elements is arrayed two-dimensionally, a housing that houses the sensor panel, and a detector that detects triaxial acceleration applied to the housing;
- an integrator that integrates a temporal change of acceleration in each axis which acceleration is detected by the detector;
- a normalization processor that normalizes an integration value of the acceleration in each axis which value is by the integrator; and
- a determiner that classifies the numeric value of each axis, which value is normalized by the normalization processor, by a first threshold and determines an impact part on the housing on the basis of a result of the classification for each axis.

12. The radiography image photographing system according to claim 11, wherein the integrator integrates a temporal change of the acceleration in a predetermined certain period.

13. The radiography image photographing system according to claim 11, wherein the first threshold for classification of the numeric value normalized by the normalization processor is individually determined for each axis.

14. The radiography image photographing system according to claim 11, wherein the first threshold is 0.41 or smaller.

15. The radiography image photographing system according to claim 14, wherein the first threshold is 0.3 or smaller.

16. The radiography image photographing system according to claim 11, wherein the detector is arranged at a center part of the housing when seen in a radiation incident direction.

17. The radiography image photographing system according to claim 11, further comprising an impact history part that adds and accumulates, for each impact part on the housing, an impact determination value based on detection by the detector.

18. The radiography image photographing system according to claim 17, wherein the impact determination value is added and accumulated by the impact history part in a case of being larger than a second threshold.

19. The radiography image photographing system according to claim 17, further comprising an annunciation processor that performs annunciation processing in a case where an accumulation value of the impact determination value, which is added and accumulated by the impact history part, with respect to any impact part exceeds a third threshold.

20. A radiography image photographing system comprising:
- a radiography image photographing device including a sensor panel in which a plurality of radiation detection elements is arrayed two-dimensionally, a housing that houses the sensor panel, and a detector that detects impact applied to the housing;
- a determiner that determines an impact part on the housing on the basis of the detection by the detector; and
- an impact history part that adds and accumulates, for each impact part on the housing, an impact determination value based on the detection by the detector.

* * * * *